(12) United States Patent
Nakatani et al.

(10) Patent No.: US 8,637,078 B2
(45) Date of Patent: Jan. 28, 2014

(54) BILAYER TABLET COMPRISING TELMISARTAN AND DIURETIC

(75) Inventors: Manabu Nakatani, Kawanishi (JP); Kazutoshi Yokoyama, Sakai (JP); Takeshi Sawada, Ikeda (JP)

(73) Assignee: Boehringer Ingelheim International GmbH, Ingelheim (DE)

( * ) Notice: Subject to any disclaimer, the term of this patent is extended or adjusted under 35 U.S.C. 154(b) by 1193 days.

(21) Appl. No.: 11/560,059

(22) Filed: Nov. 15, 2006

(65) Prior Publication Data

US 2008/0113023 A1 May 15, 2008

(30) Foreign Application Priority Data

Nov. 24, 2005 (EP) .................................. 05025601

(51) Int. Cl.
*A61K 9/24* (2006.01)
*A61K 9/16* (2006.01)
*A61K 9/50* (2006.01)

(52) U.S. Cl.
USPC .......................................... 424/472; 424/494

(58) Field of Classification Search
None
See application file for complete search history.

(56) References Cited

U.S. PATENT DOCUMENTS

| 4,735,954 A * | 4/1988 | Irikura et al. .................. 514/332 |
| 5,629,316 A * | 5/1997 | Kurihara et al. ......... 514/263.32 |
| 5,697,922 A | 12/1997 | Thombre |
| 5,861,173 A * | 1/1999 | Nishioka et al. .............. 424/480 |
| 6,071,939 A | 6/2000 | Gaviraghi et al. |
| 2004/0028505 A1 | 2/2004 | Bilbrey |
| 2004/0110813 A1 * | 6/2004 | Nakatani et al. .............. 514/394 |
| 2005/0089575 A1 * | 4/2005 | Friedl et al. ................... 424/474 |

FOREIGN PATENT DOCUMENTS

| AU | 655794 A1 | 2/1992 |
| CA | 2 524 091 A1 | 11/2004 |
| EP | 1054019 A1 * | 11/2000 |
| FR | 2 787 330 A1 | 6/2000 |
| WO | 0027397 A1 | 5/2000 |
| WO | 0043370 A1 | 7/2000 |
| WO | 03059327 A1 | 7/2003 |
| WO | 2004096215 A1 | 11/2004 |
| WO | 2005014043 A1 | 2/2005 |
| WO | 2006063737 A1 | 6/2006 |

OTHER PUBLICATIONS

Micardis HCT (Telmisartan and Hydrochlorothiazide) tablets, 40mg/12.5 mg 80 mg/12.5 mg and 80 mg/25 mg; (2004) http://www.fda.gov.medwatch/SAFETY/2004/apr-PI/MicardisHCT_PI.pdf>.
International Search Report for PCT/EP03/10382 mailed on Jan. 19, 2004.
International Search Report for PCT/EP2006/068737 mailed on Jul. 30, 2007.
Disclosure of Prior Art Sale Under § 102(b) No date; 1 page.

* cited by examiner

*Primary Examiner* — Juliet Switzer
*Assistant Examiner* — Caralynne Helm
(74) *Attorney, Agent, or Firm* — Michael P. Morris; Mary-Ellen Devlin; Usha R. Patel

(57) ABSTRACT

The invention relates to a bilayer pharmaceutical tablet comprising a first layer containing 3 to 50 wt. % of telmisartan dispersed in a dissolving tablet matrix and a second layer containing a diuretic in a disintegrating tablet matrix as well as a processes for producing same.

3 Claims, No Drawings

BILAYER TABLET COMPRISING TELMISARTAN AND DIURETIC

FIELD OF THE INVENTION

The present invention relates to an alternative bilayer pharmaceutical tablet formulation comprising the angiotensin II receptor antagonist telmisartan e.g. in form of granules or in form of a powder in combination with a diuretic such as hydrochlorothiazide (HCTZ). It further provides a method of producing said bilayer tablet.

BACKGROUND OF THE INVENTION

INN Telmisartan is an angiotensin II receptor antagonist developed for the treatment of hypertension and other medical indications as disclosed in EP-A-502314. Its chemical name is 4'-[2-n-propyl-4-methyl-6-(1-methylbenzimidazol-2-yl)-benzimidazol-1-ylmethyl]-biphenyl-2-carboxylic acid having the following structure:

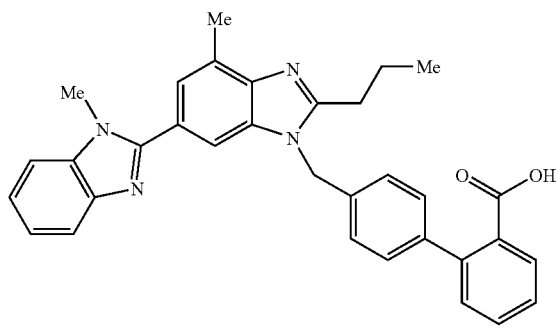 [SMILES: CCCc1nc2c(C)cc(-c3nc4ccccc4n3C)cc2n1Cc1ccc(-c2ccccc2C(=O)O)cc1]

Telmisartan is generally manufactured and supplied in the free acid form. As disclosed in WO 00/43370, crystalline telmisartan exists in two polymorphic forms having different melting points. Under the influence of heat and humidity, the lower melting polymorph B transforms irreversibly into the higher melting polymorph A. Both forms are characterized by a very poor solubility in aqueous systems at the physiological pH range of the gastrointestinal tract of between pH 1 to 7.

Telmisartan is obtainable on the market under the trade name Micardis®. Starting from the free acid form Telmisartan as introduced to the market is manufactured using an expensive spray-drying process. Due to the poor solubility of the free acid form preparation of alternative telmisartan formulation is difficult.

Diuretics such as amiloride, chlorothalidone, furosemide, hydrochlorothiazide, indapamide and piretanide are therapeutic agents used in the treatment of edema and hypertension. Occasionally they are combined with anti-hypertensive agents acting on the basis of a different mode of action to achieve synergistic therapeutic efficacy in the treatment of hypertension. A preferred diuretic is hydrochlorothiazide (HCTZ). The chemical name of HCTZ is 6-chloro-3,4-dihydro-2H-1,2,4-benzothiadiazine-7-sulfonamide-1,1-dioxide having the following structure

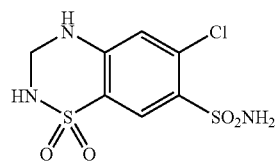 [SMILES: NS(=O)(=O)c1cc2c(cc1Cl)NCNS2(=O)=O]

It is an object of the present invention to provide a fixed dose combination drug comprising telmisartan and a diuretic such as HCTZ displaying the required fast dissolution and immediate drug release profile combined with adequate stability. Generally, a fixed-dose combination of drugs intended for immediate release is prepared by either making a powder mixture or a co-granulate of the two active ingredients with the necessary excipients, normally keeping the basic formulation of the corresponding mono-drug preparation and simply adding the second drug component.

With a combination of telmisartan and HCTZ, this approach was not feasible due to the incompatibility of HCTZ with basic compounds such as, e.g., meglumine (N-methyl-D-glucamine) which is a component of conventional telmisartan formulations, and the reduced dissolution rate of HCTZ from a dissolving matrix as compared with dissolution from a disintegrating tablet matrix.

Several galenical approaches to overcome the incompatibility problem have been investigated. A classical approach is to coat the HCTZ particles in a fluidized-bed granulator with a polymer solution containing water soluble polymers like hydroxypropylcellulose, hydroxypropylmethylcellulose or polyvinylpyrrolidone, thereby reducing the contact surface area of the HCTZ particles with the telmisartan formulation during mixing and compressing. Yet, by these means it was not possible to reduce the contact area of HCTZ with the telmisartan formulation in a compressed tablet to a degree sufficient to achieve the desired prolonged shelf life.

Furthermore, the dissolution rate of HCTZ from tablets comprising coated HCTZ in a telmisartan formulation was further reduced due to the gel-forming properties of the polymer.

Another approach was to produce separate film-coated tablets for telmisartan and HCTZ in such a size and shape that these could be filled into a capsule. By dividing the doses into two to four single small tablets for telmisartan and into one or two small tablets for HCTZ, a capsule of size 1 to 0 long could be filled. Yet, with this approach the drug dissolution rate of telmisartan was reduced compared to the single entities due to a lag-time effect of the large capsule shells. Furthermore, with regard to patients' compliance a zero long capsule is not deemed reliable.

BRIEF SUMMARY OF THE INVENTION

In accordance with the present invention, is has now been found that the above-described problems associated with conventional approaches in the preparation of a fixed dose combination drug comprising telmisartan and a diuretic can be solved by means of a bilayer pharmaceutical tablet comprising a first layer containing 3 to 50 wt. % of telmisartan dispersed in a dissolving tablet matrix comprising
 (a) a basic agent in a molar ratio of basic agent:telmisartan=1:1 to 10:1,
 (b) a surfactant or emulsifier in an amount of about 1 to 20 wt. % of the final composition,
 (c) 25 to 70 wt. % of a water-soluble diluent, and (d) optionally 0 to 20 wt. % of further excipients and/or adjuvants, and a second tablet layer containing a diuretic in a disintegrating tablet matrix.

The bilayer tablet according to the present invention provides a largely pH-independent dissolution of the poorly water-soluble telmisartan, thereby facilitating dissolution of the drug at a physiological pH level, and also provides for immediate release of the diuretic from the fast disintegrating matrix. At the same time, the bilayer tablet structure overcomes the stability problem caused by the incompatibility of diuretics like HCTZ with basic constituents of the telmisartan formulation.

In a further aspect, the present invention relates to the process of producing the bilayer tablet according to the invention.

DETAILED DESCRIPTION OF THE INVENTION

It is known from WO 2004/028505 that the solubility of telmisartan can be raised by a factor of several hundred by a pharmaceutical composition comprising 3 to 50 wt. % of telmisartan dispersed in a dissolving matrix comprising (a) a basic agent in a molar ratio of basic agent:telmisartan=1:1 to 10:1,
(b) a surfactant or emulsifier in an amount of about 1 to 20 wt. % of the final composition,
(c) 25 to 70 wt. % of a water-soluble diluent, and
(d) optionally 0 to 20 wt. % of further excipients and/or adjuvants, the sum of all components adding to 100%.

The problem of a known incompatibility of diuretics such as HCTZ with basic compounds such as meglumine which are a component of the conventional telmisartan formulation can be solved by preparing bilayer tablets according to the present invention, which keep the incompatibility under control.

The term "dissolving tablet matrix" refers to a pharmaceutical tablet base formulation having immediate release (fast dissolution) characteristics that readily dissolves in a physiological aqueous medium.

The active ingredient telmisartan is generally supplied in its free acid form, although pharmaceutically acceptable salts may also be used. It is preferred to remove agglomerates from the starting material, e.g. by sieving, in order to facilitate wetting and dissolution during further processing.

Substantially amorphous telmisartan may be produced by any suitable method known to those skilled in the art, for instance, by freeze drying of aqueous solutions, coating of carrier particles in a fluidized bed, and solvent deposition on sugar pellets or other carriers. Preferably, however, telmisartan is prepared by the conventional wet granulation methods such as fluid bed granulation.

Specific examples of suitable basic agents are alkali metal hydroxides such as NaOH and KOH; furthermore $NaHCO_3$, $KHCO_3$, $Na_2CO_3$, $K_2CO_3$, $Na_2HPO_4$, $K_2HPO_4$; basic amino acids such as arginine; and meglumine (N-methyl-D-glucamine).

The surfactants and emulsifiers may be ionic or non-ionic, the latter being preferred. Specific examples of surfactants and emulsifiers are such as poloxamers or pluronics, polyethylene glycols, polyethylene glycol monostearate, polysorbates, sodium lauryl sulfate, polyethoxylated and hydrogenated castor oil etc.

With regard to the poloxamers or pluronics suitable as non-ionic surfactants and emulsifiers is referred to the definition given in The Merck Index, $12^{th}$ edition, 1996 being herewith incorporated by reference. Suitable poloxamers may have an average mol weight of about 2000 to 12000, preferably 4000 to 10000, more preferred 6000 to 10000, most preferred 8000 to 9000. Examples for specific poloxamers are poloxamer 182LF, poloxamer 331 and poloxamer 188.

Specific examples of suitable water-soluble diluents are carbohydrates such as monosaccharides like glucose; oligosaccharides like sucrose; and sugar alcohols like erythritol, sorbitol, mannitol, dulcitol, ribitol and xylitol. Mannitol, erythritol, sorbitol and sucrose are preferred diluents.

The other excipients and/or adjuvants are, for instance, selected from binders, carriers, lubricants, flow control agents, crystallization retarders, solubilizers and coloring agents.

The binder may be selected from the group of dry binders and/or the group of wet granulation binders, depending on the manufacturing process chosen for the pharmaceutical composition. Suitable dry binders are, e.g., cellulose powder, crystalline cellulose, microcrystalline cellulose or light anhydrous silicic acid. Specific examples of wet granulation binders are corn starch, polyvinyl pyrrolidone (Povidone), vinylpyrrolidone-vinylacetate copolymer (Copovidone) and cellulose derivatives like hydroxymethylcellulose, hydroxyethylcellulose, hydroxypropyl-cellulose and hydroxypropyl-methylcellulose.

Suitable disintegrants are, e.g., sodium starch glycolate, Crospovidon, Croscarmellose, sodium carboxymethylcellulose and dried corn starch.

The other excipients and adjuvants, if used, are preferably selected from diluents and carriers such as cellulose powder, crystalline cellulose or microcrystalline cellulose, cellulose derivatives like hydroxymethylcellulose, hydroxyethylcellulose, hydroxypropylcellulose and hydroxy-propylmethylcellulose, dibasic calcium phosphate, corn starch, pregelatinized starch, polyvinyl pyrrolidone (Povidone) etc.; lubricants such as stearic acid, magnesium stearate, sodium stearylfumarate, glycerol tribehenate, etc.; flow control agents such as colloidal silica, light anhydrous silicic acid, crystalline cellulose, talc, etc.; crystallization retarders such as Povidone, etc.; coloring agents, including dyes and pigments such as Iron Oxide Red or Yellow, titanium dioxide, talc, etc.; and mixtures of two or more of these excipients and/or adjuvants.

The first tablet layer containing telmisartan according to the present invention provides solubilization of the poorly water-soluble telmisartan of up to a concentration of more than 4.4 mg/100 mL, thereby facilitating dissolution of the drug at a physiological pH level, and also provides for immediate release from the fast disintegrating matrix.

The presence of component (b), a surfactant or emulsifier, is essential to achieve this dissolution of the active ingredient as well as for the use of a simplified manufacture process such as fluid-bed granulation instead of spray-drying for preparing a bilayer tablet layer according to the invention.

In a preferred embodiment the pharmaceutical composition according to the invention comprises 10 to 35 wt. % of telmisartan dispersed in a dissolving matrix comprising (a) a basic agent, in a molar ratio of basic agent:telmisartan=1.5:1 to 5:1,
(b) a non-ionic surfactant or emulsifier, in an amount of about 1 to 10 wt. % of the final composition,
(c) 35 to 60 wt. % of a water-soluble diluent, and
(d) optionally 0 to 20 wt. % of further excipients and/or adjuvants, the sum of all components adding to 100%.

All specified components (a) to (d) mentioned hereinbefore may be used in the preferred embodiment, whereas preferred basic agents are NaOH, KOH, arginine and meglumine, preferred non-ionic surfactants or emulsifiers are selected from poloxamers, polyethylene glycols, polyethoxylated and hydrogenated castor oil, preferred water-soluble diluents are selected from sucrose, erythritol, sorbitol, mannitol and xylitol, and preferred optional further excipients and/or adjuvants are selected from crystalline cellulose, light anhydrous silicic acid, hydroxymethylcellulose, hydroxyethylcellulose, hydroxypropyl-cellulose, hydroxypropylmethylcellulose, magnesium stearate, corn starch, polyvinyl pyrrolidone, vinylpyrrolidone-vinylacetate copolymer, stearic acid, magnesium stearate, sodium stearylfumarate, colloidal silica, talc, povidone and coloring agents.

In a more preferred embodiment the pharmaceutical composition according to the invention comprises 15 to 25 wt. % of telmisartan dispersed in a dissolving matrix comprising
(a) a basic agent, in a molar ratio of basic agent:telmisartan=2:1 to 3:1,
(b) a non-ionic surfactant or emulsifier, in an amount of about 2 to 7 wt. % of the final composition,
(c) 35 to 50 wt. % of a water-soluble diluent, and
(d) optionally 0 to 20 wt. % of further excipients and/or adjuvants,
the sum of all components adding to 100%.

All specified components (a) to (d) mentioned hereinbefore may be used in the more preferred embodiment, whereas
the most preferred basic agent is meglumine,
the most preferred non-ionic surfactants are selected from poloxamers,
the most preferred water-soluble diluents are selected from mannitol, erythritol, sorbitol and sucrose, and
the most preferred optional further excipients and/or adjuvants are selected from crystalline cellulose, light anhydrous silicic acid and magnesium stearate.

In any embodiment of the invention one or more of the non-ionic surfactants or emulsifiers, water-soluble diluents and excipients and/or adjuvants may be present.

The second tablet layer composition contains a diuretic in a fast disintegrating tablet matrix. In a preferred embodiment, the disintegrating tablet matrix comprises a filler, a binder, a disintegrant and, optionally, other excipients and adjuvants. The diuretic is usually employed as a fine-crystalline powder, optionally in fine-milled, peg-milled or micronized form. For instance, the particle size distribution of hydrochlorothiazide, as determined by the method of laser light scattering in a dry dispersion system (Sympatec Helos/Rodos, focal length 100 mm) is preferably as follows:

$d_{10}$: ≤20 μm, preferably 2 to 10 μm
$d_{50}$: 5 to 50 μm, preferably 10 to 30 μm
$d_{90}$: 20 to 100 μm, preferably 40 to 80 μm The filler is preferably selected from D-mannitol, erytthritol, anhydrous lactose, spray-dried lactose and lactose monohydrate.

The binder is selected from the group of dry binders and/or the group of wet granulation binders, depending on the manufacturing process chosen for the second tablet layer. Suitable dry binders are, e.g., cellulose powder and microcrystalline cellulose. Specific examples of wet granulation binders are corn starch, polyvinyl pyrrolidone (Povidon), vinylpyrrolidone-vinylacetate copolymer (Copovidone) and cellulose derivatives like hydroxymethylcellulose, hydroxyethylcellulose, hydroxypropyl-cellulose and hydroxypropylmethylcellulose.

Suitable disintegrants are, e.g., sodium starch glycolate, Crospovidon, Croscarmellose, sodium carboxymethylcellulose and dried corn starch, sodium starch glycolate being preferred.

The other excipients and adjuvants, if used, are preferably selected from diluents and carriers such as cellulose powder, microcrystalline cellulose, cellulose derivatives like hydroxymethylcellulose, hydroxyethylcellulose, hydroxypropylcellulose and hydroxy-propylmethylcellulose, dibasic calcium phosphate, corn starch, pregelatinized starch, polyvinyl pyrrolidone (Povidone) etc.; lubricants such as stearic acid, magnesium stearate, sodium stearylfumarate, glycerol tribehenate, etc.; flow control agents such as colloidal silica, talc, etc.; crystallization retarders such as Povidone, etc.; solubilizers such as Pluronic, Povidone, etc.; coloring agents, including dyes and pigments such as Iron Oxide Red or Yellow, titanium dioxide, talc, etc.; pH control agents such as citric acid, tartaric acid, fumaric acid, sodium citrate, dibasic calcium phosphate, dibasic sodium phosphate, etc.; surfactants and emulsifiers such as Pluronic, polyethylene glycols, sodium carboxymethyl cellulose, polyethoxylated and hydrogenated castor oil, etc.; and mixtures of two or more of these excipients and/or adjuvants.

The second tablet layer composition generally comprises 1.5 to 35 wt. %, preferably 2 to 25 wt. %, of active ingredient; 25 to 85 wt. %, preferably 35 to 75 wt. %, of filler; 1 to 40 wt. %, preferably 10 to 30 wt. %, of binder; 0.5 to 10 wt. %, preferably 1 to 5 wt. %, of wet granulation binder; and 1 to 10 wt. %, preferably 2 to 8 wt. %, of disintegrant. The other excipients and adjuvants are generally employed in the same amount as in the first tablet layer composition.

The tablets so obtained can be further processed using conventional techniques, for instance can be coated using suitable coatings known in the art which do not negatively affect the dissolution properties of the final formulation. For instance the tablets can be provided with a film coat for moisture protection by film forming polymers such as polyvinyl alcohol, hydroxypropyl cellulose, ethylcellulose, polyvinylacetal diethylaminoacetate and polymeric methacrylates together with plasticizers such as polyethylene glycols onto the core tablets. Even though the polymer is water soluble, its rate of solution is slow enough to afford the core tablets moisture protection. Other polymers, which offer similar water solubility and a similar degree of moisture protection may also be used.

Additionally, agents such as beeswax, shellac, cellulose acetate phthalate, polyvinyl acetate phthalate, zein, can be dissolved in a suitable solvent together with plasticizers such as polyethylene glycol and applied to the tablets, provided that the coating has no substantial effect on the disintegration/dissolution of the dosage form and that the coated dosage form is physiochemically stable.

After the dosage form is coated, a sugar coating may be applied onto the sealed pharmaceutical dosage form. The sugar coating may comprise sucrose, dextrose, sorbitol and the like or mixtures thereof. If desired, colorants or opacifiers may be added to the sugar solution.

Flow control agents are preferably not added for production of tablet formulations according to the present invention since these agents, in combination with the high compression forces used in tablet production, deteriorate dissolution or disintegration of the tablets. Therefore, in tablet formulations the content of the further excipients and/or adjuvants will preferably be in the lower range, e.g. in the range of 0.1 to 5 wt. %, preferably 0.3 to 2 wt. %, of the final formulation since only low amounts of lubricants should be present.

The bilayer tablet according to the present invention generally contains 10 to 160 mg, preferably 40 to 80 mg, of telmisartan and 5 to 50 mg, preferably 6.25 to 25 mg, of diuretic. Presently preferred forms are bilayer tablets comprising 40/6.25 mg, 40/12.5 mg, 80/12.5 mg and 80/25 mg of telmisartan and HCTZ, respectively.

For instance, the total composition of the telmisartan layer according to the invention may vary within the following ranges, with the proviso that the proportional composition given above with respect to the basic pharmaceutical compositions is met:

10 to 160 mg of telmisartan;
10 to 160 mg of meglumine or arginine, or
2 to 33 mg of NaOH, or
3 to 46 mg of KOH, or
4 to 80 mg of $NaHCO_3$, $KHCO_3$, $Na_2CO_3$, $K_2CO_3$, $Na_2HPO_4$ or $K_2HPO_4$;
2 to 100 mg of non-ionic surfactants or emulsifiers;
20 to 400 mg of water soluble diluents; and
0 to 80 mg of further excipients and/or adjuvants;

preferably 20 to 80 mg of telmisartan;
10 to 90 mg of meglumine, or
4 to 16 mg of NaOH, or
6 to 23 mg of KOH;
2 to 40 mg of non-ionic surfactants or emulsifiers selected from poloxamers, polyethylene glycols, polyethoxylated and hydrogenated castor oil, poloxamers being especially preferred;
40 to 200 mg of water soluble diluents selected from glucose, sucrose, erythritol, sorbitol, mannitol and xylitol; and
0.1 to 40 mg of further excipients and/or adjuvants selected from crystalline cellulose, light anhydrous silicic acid, hydroxymethylcellulose, hydroxyethylcellulose, hydroxypropyl-cellulose, hydroxypropylmethylcellulose, magnesium stearate, corn starch, polyvinyl pyrrolidone, vinylpyrrolidone-vinylacetate copolymer, stearic acid, magnesium stearate, sodium stearylfumarate, colloidal silica, talc, povidone and coloring agents;

and most preferred 40 to 80 mg of telmisartan;
20 to 80 mg of meglumine;
5 to 30 mg of non-ionic surfactants or emulsifiers selected from poloxamers, poloxamer 188 being especially preferred;
70 to 180 mg of water soluble diluents selected from mannitol, erythritol, sorbitol and sucrose; and
0.1 to 20 mg of further excipients and/or adjuvants selected from crystalline cellulose, light anhydrous silicic acid and magnesium stearate.

HCTZ is incompatible with basic agents being a component of the telmisartan tablet formulations according to the invention. This problem can be overcome by means of a bilayer pharmaceutical tablet comprising a first telmisartan containing tablet layer prepared from a pharmaceutical composition mentioned hereinbefore under the first aspect of the invention, and a second tablet layer containing a diuretic in a disintegrating tablet matrix.

The second tablet layer composition generally comprises 1.5 to 35 wt. %, preferably 2 to 25 wt. %, of active ingredient; 25 to 85 wt. %, preferably 35 to 75 wt. %, of filler; 10 to 40 wt. %, preferably 10 to 30 wt. %, of dry binder; 0.5 to 10 wt. %, preferably 1 to 5 wt. %, of wet granulation binder; and 1 to 10 wt. %, preferably 2 to 8 wt. %, of disintegrant. The other excipients and adjuvants are generally employed in the same amount as in the first tablet layer composition. The filler is may be selected from D-mannitol, erytthritol, anhydrous lactose, spray-dried lactose and lactose monohydrate.

Tablets of the present invention tend to be very low hygroscopic and may be packaged using PVC-blisters, PVC/PVDC-blisters or a moisture-proof packaging material such as aluminium foil blister packs, polypropylene tubes, glass bottles and HDPE bottles.

A further object of the invention is directed to methods for producing the bilayer tablets hereinbefore. The tablet layers comprising telmisartan according to the invention may be prepared by any suitable method known to those skilled in the art, for instance, by freeze drying of aqueous solutions, coating of carrier particles in a fluidized bed, and by solvent deposition on sugar pellets or other carriers. Preferably, however, the pharmaceutical compositions are prepared using a granulation process, e.g. the fluid-bed granulation process (A), or, in the alternative, the spray-drying process (B) described specifically hereinafter. The less complicated and cheaper fluid-bed granulation process (A) is preferred.

Since during subsequent processing telmisartan is normally dissolved and transformed into a substantially amorphous form, its initial crystal morphology and particle size are of little importance for the physical and biopharmaceutical properties of the pharmaceutical composition obtained.

In a first embodiment a fluid-bed granulation process (A) can be used for preparation of the pharmaceutical compositions according to the invention, characterized by the following steps:

(i) preparing a granulation liquid as an aqueous solution by dissolving 3 to 50 wt. % of telmisartan together with the following components in water or in a mixture solution of ethanol and water:
  (a) a basic agent in a molar ratio of basic agent:telmisartan=1:1 to 10:1,
  (b) a non-ionic surfactant or emulsifier in an amount of about 1 to 20 wt. %,
(ii) placing 25 to 70 wt. % of a water-soluble diluent into a fluid-bed granulator, optionally together with 10 to 20 wt. % of a dry binder, including a premix-step,
(iii) carrying out the fluid-bed granulation using the granulation liquid for spraying onto the components placed into the granulator,
(iv) after completion of the granulation drying and, optionally, screening the granulate obtained,
(v) optionally blending the granulate with further excipients and/or adjuvants in order to prepare the final composition, and
(vi) optionally milling the granulate thus obtained in order to produce a powdery composition of defined particle size distribution;

wherein all percentage amounts given are related to the final composition to be prepared.

Preferred embodiments of the process with regard to specific components and proportional amounts fully correspond to those disclosed hereinbefore with regard to the first aspect of the invention.

In the premix step of step (ii) an inlet air temperature of about 60 to 120° C. may be used.

In the granulation step (iii) an inlet temperature of about 80 to 100° C. may be used. The spraying rate greatly depends on the type of granulator used as well as the batch size and can be adjusted by the skilled person by routine. Only for instance, a spraying rate of 400 to 1000 mL/min may be suitable for a 200 kg granulate batch. Lower or higher spray rates may also be used.

In the drying step of step (iv) an inlet temperature of about 60 to 120° C., and a duration of drying of about 1 to 30 minutes may be used.

In the screening step of step (iv) a screen with a mesh size of 0.5 to 3 mm may be suitable.

The optional milling step (vi) can be carried out conventionally by the skilled person.

In a second embodiment a spray-drying process (B) can be used for preparation of the pharmaceutical compositions according to the invention, characterized by the following steps:
(i) preparing an aqueous spray-solution by dissolving 3 to 50 wt. % of telmisartan together with the following components in water or mixture solution of ethanol and water:
    (a) a basic agent in a molar ratio of basic agent:telmisartan=1:1 to 10:1,
    (b) a non-ionic surfactant or emulsifier in an amount of about 1 to 20 wt. %,
(ii) spray-drying said aqueous spray-solution to obtain a spray-dried granulate;
(iii) mixing said spray-dried granulate with 25 to 70 wt. % of a water-soluble diluent to obtain a premix;
(iv) optionally, mixing said premix with a lubricant;
(v) optionally, adding further excipients and/or adjuvants in any of steps (i) to (iv),
wherein all percentage amounts given are related to the final composition to be prepared.

If it is necessary to adjust a particular particle size distribution in a powdery composition thus obtained a conventional milling step may be applied, preferably before optional addition of a lubricant according to step (iv). Furthermore, a powdery composition may be converted into a granular composition applying conventional granulation techniques.

Preferred embodiments of the process with regard to specific components and proportional amounts fully correspond to those disclosed hereinbefore with regard to the first aspect of the invention.

In a preferred embodiment of process (B), an aqueous alkaline solution of telmisartan is prepared by dissolving the active ingredient in water or mixture solution of ethanol and water with the help of one or more basic agents like sodium hydroxide or meglumine. Optionally, a recrystallization retarder may be added. The dry matter content of the starting aqueous solution is generally 10 to 40 wt. %, preferably 20 to 30 wt. %.

The aqueous solution is then spray-dried at room temperature or preferably at increased temperatures of, for instance, between 50 and 100° C. in a co-current or counter-current spray-drier at a spray pressure of, for instance, 1 to 4 bar. Generally speaking, the spray-drying conditions are preferably chosen in such a manner that a spray-dried granulate having a residual humidity of $\leq 5$ wt. %, preferably $\leq 3.5$ wt. %, is obtained in the separation cyclone. To that end, the outlet air temperature of the spray-drier is preferably kept at a value of between about 80 and 90° C. while the other process parameters such as spray pressure, spraying rate, inlet air temperature, etc. are adjusted accordingly.

The spray-dried granulate obtained is preferably a fine powder having the following particle size distribution:
$d_{10}$: $\leq 20$ µm, preferably $\leq 10$ µm
$d_{50}$: $\leq 80$ µm, preferably 20 to 55 µm
$d_{90}$: $\leq 350$ µm, preferably 50 to 150 µm After spray-drying, the active ingredient (telmisartan) as well as the excipients contained in the spray-dried granulate are in a substantially amorphous state with no crystallinity being detectable. From a physical point of view, the spray-dried granulate is a solidified solution or glass having a glass transition temperature Tg of preferably >50° C., more preferably >80° C.

The lubricant is generally added to the premix in an amount of 0.1 to 5 wt. %, preferably 0.3 to 2 wt. %, based on the weight of the final composition.

Mixing is carried out in two stages, i.e. in a first mixing step the spray-dried granulate and the diluent are admixed using, e.g., a high-shear mixer or a free-fall blender, and in a second mixing step the lubricant is blended with the premix, preferably also under conditions of high shear. The method of the invention is however not limited to these mixing procedures and, generally, alternative mixing procedures may be employed in any steps of the process comprising a mixing procedure, such as, e.g., container mixing with intermediate screening.

Batches of granulates with different composition obtained by process (A) or (B) may be blended together in order to adjust a target composition and may additionally be blended with further excipients and/or adjuvants such as lubricants, if required for adjusting a final composition for further processing into the final formulation ready for use/ingestion, for instance for filling into capsules using a suitable capsule filling machine or for direct compression of tablets using a suitable rotary tablet press.

For direct compression, the final composition may be prepared by dry-mixing the constituent components, e.g. by means of a high-intensity mixer or a free-fall blender. Alternatively, the final composition may be prepared using a wet granulation technique wherein an aqueous solution of a wet granulation binder is added to a premix and subsequently the wet granulate obtained is dried, e.g. in a fluidized-bed dryer or drying chamber. The dried mixture is screened and then a lubricant is admixed, e.g. using a tumbling mixer or free-fall blender, whereafter the composition is ready for compression.

A bilayer tablet mentioned under the second aspect of the invention can be prepared by the following process:
(i) providing a first tablet layer composition comprising telmisartan by use of the fluid-bed granulation process (A) or the spray-drying process (B) described hereinbefore,
(ii) providing a second tablet layer composition by
    a) mixing, granulating, drying and screening a diuretic with the constituents of a disintegrating tablet matrix and, optionally, further excipients and/or adjuvants;
    b) admixing a lubricant to obtain a final blend for the second tablet layer;
(iii) introducing the first or the second tablet layer composition in a tablet press;
(iv) compressing said tablet layer composition to form a tablet layer;
(v) introducing the other tablet layer composition into the tablet press; and
(vi) compressing both tablet layer compositions to form a bilayer tablet.

For preparing the bilayer tablet according to the present invention, the first and second tablet layer compositions may be compressed in the usual manner in a bilayer tablet press, e.g. a high-speed rotary press in a bilayer tableting mode. However, care should be taken not to employ an excessive compression force for the first tablet layer. Preferably, the ratio of the compression force applied during compression of the first tablet layer to the compression force applied during compression of both the first and second tablet layers is in the range of from 1:10 to 1:2. For instance, the first tablet layer may be compressed at moderate force of 1 to 10 kN, whereas the main compression of first plus second layer is performed at a force of 8 to 30 kN.

During bilayer tablet compression adequate bond formation between the two layers is achieved by virtue of distance attraction forces (intermolecular forces) and mechanical interlocking between the particles.

In order to avoid any cross-contamination between the first and second tablet layers (which could lead to decomposition of HTCZ), any granulate residues have to be carefully removed during tableting by intense suction of the die table within the tableting chamber.

The bilayer tablets obtained release the active ingredients rapidly and in a largely pH-independent fashion, with complete release occurring within less than 60 min and release of the major fraction occurring within less than 45 min. The dissolution/-disintegration kinetics of the bilayer tablet may be controlled in different ways. For instance, both layers may dissolve/disintegrate simultaneously. Preferably, however, the second tablet layer containing the diuretic disintegrates first whereas the first tablet layer containing telmisartan dissolves in parallel or subsequently. Normally, at least 80% and typically at least 90% of the drug load are dissolved after 45 min.

In order to further illustrate the present invention, the following non-limiting examples are given:

EXAMPLES

Example 1: Formulation example telmisartan + HCTZ

|  | T40 + H12.5 FDC | T80 + H12.5 FDC |
|---|---|---|
| BIBR277SE | 40 mg | 80 mg |
| Meglumine | 40 mg | 80 mg |
| Poloxamer 188 | 8 mg | 16 mg |
| D-mannitol | 80.5 mg | 161 mg |
| Iron oxide yellow | 0.14 mg | 0.28 mg |
| Magnesium stearate | 1.5 mg | 3 mg |
| HCTZ | 12.5 mg | 12.5 mg |
| D-mannitol | 43 mg | 98.5 mg |
| Crystalline cellulose | 11 mg | 22 mg |
| HPC-L | 3 mg | 6 mg |
| Iron oxide yellow | 0.07 mg | 0.14 mg |
| Magnesium stearate | 0.5 mg | 1 mg |
| Total | 240 | 480 |

Example 2

Manufacturing Example for T40+H12.5 FDC

1. Telmisartan Layer
1.1 Granulation Liquid or Spray-Solution

About 10.8 kg of purified water are measured into a suitable stainless steel vessel at a temperature of between 20-40° C. In sequence, 0.96 kg of Poloxamer 188 (polyoxyethylene[160]polyoxypropylene[30]glycol), 4.8 kg of meglumine and 4.8 kg of telmisartan (mixture of polymorph A and B) are dissolved in the purified water under intensive stirring until a virtually clear solution is obtained. Total volume is about 18 L.

1.2 Granulation, Drying and Screening 9.66 kg of D-mannitol and 16.8 g of iron oxide yellow (iron oxide yellow is screened in advance) are placed into a fluid-bed granulator sprayed with 21.36 kg of granulation liquid (containing 10.56 kg of dry mass). Then is sprayed with about 0.5 L of purified water, followed by a drying step and a screening step.

Process Data Pre-Mixing:
Inlet air temperature: 80-100° C.
End of pre-mixing: Gut temperature about 65° C.
Process Data Granulation:
Inlet air temperature: 80-100° C.
Spraying rate: 50-300 g/min
Process Data Drying Step:
Inlet air temperature: 80-100° C.
End of drying: Gut temperature more than 70° C.
Duration of drying: about 5 minutes
Process Data Screening Step:
The granules are screened, for instance using an oscillator or comil screen machine, with a mesh size of 1.5 mm.

1.3 Final Mixture for Preparation of Tablet Formulation:

Two 20.2368 kg batches of screened granules are mixed using a suitable mixer with a revolution of 10 rpm for 10 to 20 min, resulting in a 40.4736 kg mixed batch which is finally blended with 360 g of magnesium stearate, using a suitable mixer with a revolution of 10 rpm for about 15 min thus producing the final mixture.

2. HCTZ Layer
2.1 Granulation Liquid or Spray-Solution

About 9 kg of purified water are measured into a suitable stainless steel vessel. In sequence, 0.72 kg of HPC-L is dissolved in the purified water under intensive stirring until a virtually clear solution is obtained.

2.2 Granulation, Drying and Screening 3 kg of HCTZ, 10.32 kg of D-mannitol, 2.64 kg of crystalline cellulose and 16.8 g of iron oxide yellow (iron oxide yellow is screened in advance) are placed into a fluid-bed granulator sprayed with 9.72 kg of granulation liquid (containing 0.72 kg of dry mass). Then is sprayed with about 0.5 L of purified water, followed by a drying step and a screening step.

Process Data Pre-Mixing:
Inlet air temperature: 80-100° C.
End of pre-mixing: Gut temperature about 60° C.
Process Data Granulation:
Inlet air temperature: 80-100° C.
Spraying rate: 200-400 g/min
Process Data Drying Step:
Inlet air temperature: 80-100° C.
End of drying: Gut temperature more than 70° C.
Process Data Screening Step:
The granules are screened, for instance using an oscillator or comil screen machine, with a mesh size of 1.5 mm.

2.3. Final Mixture for Preparation of Tablet Formulation:

16.6968 kg batch of screened granules is mixed with 120 g of magnesium stearate using a suitable mixer with a revolution of 10 rpm for 15 min thus producing the final mixture.

3. Tablet Compression

Using a suitable rotary tablet press (i.e. bi-layer and/or triple-layer tablet press) the final mixtures of telmisartan layer and HCTZ layer for tablet compression are compressed into bilayer tablets. The target weight is about 240 mg for T40+H12.5 FDC.

Process parameters for tableting for T40+H12.5 FDC:

| Tablet press | HATA HT-AP65-LSU/3L |
|---|---|
| Tableting speed | 70.000 (50.000- 100.000) tabl./h |
| Stirrer blade speed: | about 18 rpm |
| Main compression force | 10 (5- 20) KN |

The tablet hardness can be adjusted by variation of the main compression force.

What is claimed is:

1. A bilayer pharmaceutical tablet comprising:
a first layer providing a dissolving matrix containing:
- 40 mg of telmisartan,
- 40 mg of meglumine,
- 8 mg of poloxamer 188,
- 80.5 mg of D-mannitol,
- 0.14 mg of iron oxide yellow, and
- 1.5 mg of magnesium stearate;

and
a second layer providing a disintegrating tablet matrix containing:
- 12.5 mg of hydrochlorothiazide,
- 43 mg of D-mannitol,
- 11 mg of crystalline cellulose,
- 3 mg of hydroxypropylcellulose,
- 0.07 mg of iron oxide yellow, and
- 0.5 mg of magnesium stearate;

or
a first layer providing a dissolving matrix containing:
- 80 mg of telmisartan,
- 80 mg of meglumine,
- 16 mg of poloxamer 188,
- 161 mg of D-mannitol,
- 0.28 mg of iron oxide yellow, and
- 3 mg of magnesium stearate;

and
a second layer providing a disintegrating tablet matrix containing:
- 12.5 mg of hydrochlorothiazide,
- 98.5 mg of D-mannitol,
- 22 mg of crystalline cellulose,
- 6 mg of hydroxypropylcellulose,
- 0.14 mg of iron oxide yellow, and
- 1 mg of magnesium stearate.

2. The bilayer pharmaceutical tablet of claim 1, wherein the dissolving matrix has immediate release characteristics.

3. A process for preparing a bilayer tablet according to claim 1, comprising introducing the first or second layer composition into a tablet press and applying a first compression force and then introducing the other of the first or second layer composition to the tablet press and applying a second compression force to form the bilayer pharmaceutical tablet, wherein the ratio of the first compression force to the second compression force is in the range of from 1:10 to 1:2.

* * * * *

UNITED STATES PATENT AND TRADEMARK OFFICE
CERTIFICATE OF CORRECTION

PATENT NO. : 8,637,078 B2  
APPLICATION NO. : 11/560059  
DATED : January 28, 2014  
INVENTOR(S) : Nakatani et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1328 days.

Signed and Sealed this
Eleventh Day of August, 2015

Michelle K. Lee
*Director of the United States Patent and Trademark Office*